United States Patent [19]
Mellor et al.

[11] Patent Number: 5,403,450
[45] Date of Patent: Apr. 4, 1995

[54] METHOD OF WATER PURIFICATION

[75] Inventors: Robert B. Mellor, Roskilde, Denmark; Jörg Ronnenberg, Seeburg; Stefan Diekmann, Bovenden, both of Germany

[73] Assignee: Mobitec Molecular Biologische Technologie GmbH, Göttingen, Germany

[21] Appl. No.: 987,288

[22] Filed: Mar. 16, 1993

[86] PCT No.: PCT/EP91/01590
§ 371 Date: Mar. 16, 1993
§ 102(e) Date: Mar. 16, 1993

[87] PCT Pub. No.: WO 92/05117
PCT Pub. Date: Apr. 2, 1992

[30] Foreign Application Priority Data

Sep. 26, 1990 [DE] Germany ............ 40 30 488.4

[51] Int. Cl.⁶ .............................................. C02F 1/461
[52] U.S. Cl. ..................................... 204/131; 204/149; 204/153.12; 204/403; 204/409; 210/632; 435/817; 435/25; 435/26; 435/27; 435/28

[58] Field of Search ........... 204/131, 149, 403, 153.12, 204/409; 435/25, 26, 27, 28, 817; 210/632

[56] References Cited

U.S. PATENT DOCUMENTS

| | | | |
|---|---|---|---|
| 4,376,689 | 3/1983 | Nakamura et al. | 204/195 B |
| 4,464,235 | 8/1984 | Simon et al. | 204/73 R |
| 5,057,421 | 10/1991 | Hofmann et al. | 435/182 |

Primary Examiner—John Niebling
Assistant Examiner—Arun S. Phasge
Attorney, Agent, or Firm—Nikaido, Marmelstein, Murray & Oram

[57] ABSTRACT

A method for converting reducible or oxidizable substances from aqueous solution is claimed in which the aqueous solution to be treated is brought into contact with immobilized oxidoreductases, if desired, in the presence of co-immobilized electron carriers and at the same time reduction or oxidation equivalents are supplied. Furthermore a potentiometric cell, in particular a flow cell is claimed which contains an electrode body and immobilized oxidoreductases as well as, if desired, co-immobilized electron carriers.

26 Claims, 4 Drawing Sheets

◨ = Elektrodenkörper
▦ = Enzym-haltige Matrix

▨ = Elektrodenkörper
▨ = Enzym-haltige Matrix

▨ = Elektrodenkörper
▦ = Enzym-haltige Matrix

METHOD OF WATER PURIFICATION

The present invention concerns a method for converting reducible or oxidizable substances in aqueous solution.

Due to the increasing environmental pollution, the supply of pure water is becoming more and more important. In order to use water as drinking water or industrial water it is often necessary to free it of impurities or to determine the amount of impurities in an aqueous solution.

The removal of problematic substances from an aqueous solution can, on the one hand, be achieved by a number of various physicochemical methods. Examples of this are filtration, exchange chromatography and/or reverse osmosis. However, in these methods the problematic substances are not degraded but instead they concentrate in a separate area of the total system. After the separation these substances are then released again into the environment in a high concentration.

The problematic substances can, on the other hand, also be removed by biological methods i.e. by enzymatic degradation in living bacterial cells. However, this degradation in cells is associated with a number of difficulties. Thus problems occur when immobilizing live bacterial cells, the metabolic by-products of bacteria contaminate the purified water. Moreover long reaction periods are necessary in living systems because of the induction times and the large diffusion barriers which the substrate as well as the product have to overcome (e.g. the immobilization matrix and the cell membrane).

Finally the cells may also be attacked and destroyed by the problematic substances.

The object of the present invention was therefore to provide a method of water purification in which the disadvantages of the state of the art are at least partially eliminated.

The object according to the present invention is achieved by a method for converting reducible or oxidizable substances in aqueous solution in which the aqueous solution to be treated is contacted with immobilized oxidoreductases, if desired, in the presence of co-immobilized electron carriers and simultaneously reduction or oxidation equivalents are supplied which are generated by electrolysis of water.

The term "conversion" within the sense of the present invention encompasses a partial removal of reducible or oxidizable substances for water analysis as well as a complete removal for water purification. In this case the essential difference between the determination of substances for water analysis and the complete removal is that from a sample only an amount adequate for the detection of a particular substance is converted.

The use of immobilized enzymes instead of living cells obviates all the aforementioned problems which occur when using living microorganisms for water purification. Furthermore, the problematic substances do not accumulate in a section of the system as in the physicochemical purification method but rather are converted directly into an environmentally compatible form.

In the method according to the present invention the oxidation or reduction equivalents are transferred onto the problematic substances by means of immobilized biocatalysts (enzymes of the oxidoreductase group) and, if desired, additional co-immobilized electron carriers.

If the method according to the present invention is used to convert a reducible substance in an aqueous solution then electrons are transferred onto the substance to be removed, if the method according to the present invention is used to convert an oxidizable substance then in contrast electrons are transferred from the substance to be removed onto an oxidizing agent. FIG. 1 shows schematically the course of a reduction using the reduction of nitrate to nitrite as an example. The first partial step of this reaction is the transfer of reduction equivalents (in this case atomic hydrogen produced electrolytically) onto the electron carrier. From there the reduction equivalent is transferred in a second partial step onto the enzyme (nitrate reductase) and from there it is finally transferred onto the substrate (nitrate) which is reduced to nitrite in this manner. These three partial steps do in fact proceed independently of each other. The method according to the present invention links these three reactions to form a total system (see FIG. 2).

The method according to the present invention in particular serves to remove problematic substances from drinking water or waste water or to analyse drinking water or waste water. The method according to the present invention allows the conversion of substances which are selected from the group comprising (a) inorganic salts and
(b) organic compounds.

Inorganic salts which can for example be removed are nitrate, sulfate, cyanide, sulfide (or $H_2S$) and phosphate. The conversion i.e. removal or/and determination of nitrate is particularly preferred. Examples of organic substances which can be converted in aqueous solution are in particular herbicides, pesticides, oil, phenols, solvents, fats, detergents (tensides, washing agents). This means that aliphatic or aromatic hydrocarbons, halogenated hydrocarbons (e.g. dioxins), organophosphorus compounds, alcohols, ketones, phenols or similar compounds can be converted in aqueous solution by the method according to the present invention. The removal or/and determination of alcohols, in particular methanol (by oxidation), or of halogenated hydrocarbons (by reductive dehalogenation) is particularly preferred.

Apart from the complete removal of reducible and oxidizable substances from aqueous solution, the method according to the present invention also enables an analytical determination of substances. For this one can for example contact only part of a stream of water with the immobilized oxidoreductase, if desired in the presence of co-immobilized electron carriers, and simultaneously supply reduction or oxidation equivalents. The consumption of the added reduction or oxidation equivalents is directly proportional to the concentration of a substance to be determined in the stream of water. The determination of this consumption and thus the measurement of the concentration of the substance to be determined can then in turn be carried out by methods which are in fact known e.g. potentiometric or amperometric measurement.

The immobilization of oxidoreductases and, if desired, electron carriers takes place on a solid carrier material. Suitable carrier materials are known to a person skilled in the art. Plastics (nylon, polyacrylamide, polymethylacrylate, polystyrene etc.), polysaccharides (agarose, dextran etc.), silicates (sand, silica gel, glass, ceramic etc.) as well as other solids (silicon, graphite), i.e. those materials which are often used for enzyme attachment or immobilization, come for example into consideration. If the presence of co-immobilized electron carriers is necessary then these are preferably located on the same carrier material as the enzyme i.e. oxidoreductases and electron carriers are immobilized in direct molecular proximity on the solid carrier material. On the other hand, the electron carrier can also be bound directly to the immobilized enzyme or the enzyme can be bound directly to the immobilized electron carrier.

The three-dimensional macroscopic structure of the carrier material may be selected as desired. It can be cylindrical (rods, threads), flat (foils), spherical or net-shaped. The carrier material is preferably used in a finely dispersed form i.e. spherical and porous with a sphere diameter of 0.5 to 120 $\mu$m, particularly preferably of 1 to 60 $\mu$m.

The enzymes and the electron carriers can either be bound directly to the matrices by cross-linking or via chemical linker arms (spacers) with or without prior treatment of the enzymes or carrier material. Such methods are known to a person skilled in the art. It is for example possible to immobilize by means of an epoxy, cyanogen bromide, diisocyanate, sulfonyl chloride, carbodiimide or 2-fluoro-1-methylpyridiniumtoluene-4sulfonate (FMP), glutaraldehyde, EDC or another compound.

The activation of a carrier material by cyanogen bromide is described for example by Kohn and Wilcheck (Biochem. Biophys. Res. Comm. 107 (1982), 878–884). The activation of a carrier material by organic sulfonyl chlorides is also known (Nilsson and Mosbach, Biochem. Biophys. Res. Comm. 102 (1981), 449–457). A method for activating hydroxyl groups of a carrier matrix by reaction with TMP in the presence of triethylamine is described by Ngo, Bio/Technology Vol. 4 (1986), 134–137. In this process the ligand (in the case of the present invention an oxidoreductase or an electron carrier) is bound to the activated matrix via amino or thiol groups. In addition it is also known that carrier materials can be activated by carbonylation e.g. with 1,1'-carbonyldiimidazole (Hearn, Meth. Enzymol. 135 (1987), 102–113). In order to immobilize oxidoreductases and electron carriers the (activated or non-activated) carrier matrix can be reacted directly with the oxidoreductase or the electron carrier or firstly reacted with a bifunctional spacer molecule to which the oxidoreductase or the electron carrier is coupled in a second step. The diisocyanate (Biebricher and Luce, U.S. Pat. 4.177,038), glutardialdehyde (Korn et al., J. Mol. Biol. 65 (1972), 525–529) and EDC methods (Yamada et al., Biochemistry 20 (1981), 4836–4842) are used as preferred immobilization methods.

According to the invention immobilized oxidoreductases are used to convert problematic substances in aqueous solution. If one wants to convert a substance by oxidation in aqueous solution then one uses an oxidase, whereas a reductase is used for the reductive conversion of a substance. The oxidase or the reductase must have an enzymatic specificity for the substance to be converted in the water. Thus an alcohol oxidase is for example used for the oxidation of methanol. In a multi-step oxidation or reduction process several enzymes may be used simultaneously or in succession. For example a nitrate reductase is necessary for the reduction of nitrate to nitrite, a nitrite reductase for the reduction of nitrite to $N_2O$ and an $N_2O$ reductase for the reduction of $N_2O$ to $N_2$. One or several dehalogenases can be used for the reductive dehalogenation of halogenated organic compounds.

Nitrate reductase can be isolated from the fungus Aspergillus or from higher plants (Campbell in: Molecular and Genetic Aspects of Nitrate Assimilation, p. 125–154, edited by Wray and Kinghorn, Oxford Univ. Press 1989) e.g. maize (Zea mays). Nitrite and $N_2O$ reductase can be obtained as an enzyme mixture from Rhodopseudomonas sphaeroides f.sp. denitrificans (Michalski and Nickolas, Biochim. Biophys. Acta 828 (1985), 130–137; Michalski et al., Biochim. Biophys. Acta 872 (1986), 50–60). Dehalogenases can be isolated for example from microorganisms occurring in sediments (Suflita et al., Science 218 (1982), 1115–1117), from Xanthobacter autotrophicus (Janssen et al., Applied and Environmental Microbiology 49 (1985), 673–677), methane-oxidizing bacteria (Little et al., Applied and Environmental Microbiology 54 (1988), 951–956) or from Arthrobacter sp. (Scholtz et al., Applied and Environmental Microbiology 54 (1988), 3034–3038). Alcohol oxidase (EC 1.1.3.13) from yeast (Saccharomyces) can for example be used for the oxidative degradation of methanol. In this reaction formaldehyde is formed which is then degraded in two further steps by aldehyde dehydrogenase to formate and then by formate dehydrogenase to $CO_2$ and $H_2O$. However, other oxidoreductases which are suitable for the respective desired purpose can also be used in the method according to the present invention. For this purpose the respective enzymes are covalently bound to an insoluble carrier material e.g. via chemical bridges. Depending on the binding and the carrier material and enzyme, the immobilized enzymes exhibit 40 to over 100 % of their initial activity in free solution.

In an oxidation electrons are withdrawn from the substance to be oxidized while in a reduction electrons are transferred onto the substance to be reduced. Electron carriers are usually necessary for this. In physiological systems with free enzymes the electron carrier is often $NAD^+$ which can be reduced to NADH. As a rule NAD cannot fulfil this function in immobilized systems. A number of other artificial electron carriers can be used instead. These are usually dyes. Bromophenol blue, representatives of the viologen group (bipyridium dyes), methylene blue, phenazine or resazurine have for example proven to be suitable as dyes. Azure A, bromophenol blue, Cibacron blue, neutral red and safranin T have proven to be particularly suitable. For the test the selected dyes were bound to a matrix. In this process the coating density was selected so that about every second binding site of the matrix is occupied by a dye molecule. The oxidoreductase used in each case was coupled to the intervening binding sites. In doing so it was found that the properties of the total system were partly changed by the immobilization. Not every dye which can act as an electron carrier for a free oxidoreductase is also able to fulfil this function for the immobilized enzyme.

It was also found that non-poisonous food dyes are also suitable as electron carriers which are co-immobilized with the oxidoreductase for the method according to the present invention. Examples of food dyes which can act as electron carriers in an immobilized state are for instance curcumin and derivatives thereof, quinoline dyes (e.g. quinoline yellow) and patent blue dyes (e.g. patent blue V). A major advantage of using food dyes as the electron carriers for the method according to the present invention is that they have a low toxicity. This is of particular importance for those embodiments in which an aqueous solution is purified of pollutants and subsequently used as drinking water and/or for producing drinks. A further advantage of some food dyes is their low price; thus curcumin is for example considerably cheaper than methyl viologen.

In the reductive conversion of nitrate in aqueous solution, the following combinations have for example proven to be particularly suitable: Nitrate reductase from maize co-immobilized with azure A or bromophenol blue, the enzyme mixture nitrite reductase and $N_2O$ reductase co-immobilized with neutral red or safranin T.

Furthermore, combinations of nitrate reductase from maize with the co-immobilized food dyes curcumin or patent blue V and of nitrite reductase with the co-immobilized food dyes curcumin, patent blue or quinoline yellow have proven to be particularly suitable.

For other systems natural electron carriers can, however, also prove to be suitable, in particular those electron carriers which are associated with membranous enzyme complexes. Examples of natural electron carriers are: ascorbate, iron proteins (flavoproteins, ferridoxins, rubidoxin, cytochromes), flavins (FAD, FMN), pyridine nucleotides (NAD, NADP), pterines, pteridines and quinones (e.g. ubiquinone).

If a protein which already contains the electron-transferring cofactor is used as the oxidoreductase, the co-immobilization of an electron carrier is not necessary. An example of such a protein is alcohol oxidase which is a flavoprotein.

Since the method according to the present invention involves a reduction or oxidation, reduction or oxidation equivalents have to be provided. This could in principle be carried out by adding suitable chemical substances. Thus one could for example add dithionite ($S_2O_4^{2-}$) or hydrogen with a suitable catalyst (to decompose molecular hydrogen into atomic hydrogen) as a reducing agent to the aqueous solution to be purified. $H_2O_2$ or oxygen already present in the aqueous solution would for example be suitable as the oxidizing agent. However, in this chemical redox reaction problems may occur due to the toxicity ($S_2O_4^{2-}$, $H_2O_2$) of the substances used and also for reasons of cost, in particular when purifying drinking water.

The reduction or oxidation equivalents which can be regenerated are generated according to the present invention by electrochemical means in particular by electrolysis of water. The electrolytic cleavage of water produces hydroxide ions ($OH^-$) and hydronium ions ($H_3O^+$). The positively charged hydronium ions migrate towards the cathode (minus pole) where they take up an electron and decompose into water and atomic hydrogen. This atomic hydrogen is unstable and rapidly combines to form $H_2$ gas. Correspondingly the negatively charged hydroxide ions migrate towards the anode (plus pole) where they release an electron and decompose into water and atomic oxygen. However, when oxidases or reductases and, if desired, electron carriers are present in the vicinity of the cathode, a rapid oxidation or reduction of the specific substrates for the respective oxidoreductase takes place. Thus for example the immobilized dyes are reduced very rapidly at the cathode by the atomic hydrogen which is only short-lived whereby the reduction is proportional to the potential difference (up to 70 volts). In this process the effectiveness of the electron transfer depends on the size of the cathode surface.

During an electrochemical redox reaction in unbuffered systems the proton and hydroxide ion concentrations already become very large within 1 to 2 minutes. This would greatly limit the activity of an unbuffered system (due to the change in pH) since when purifying water, in particular drinking water, a buffer salt should not be added to the solution as well. Therefore the method according to the present invention is preferably carried out in a potentiometric cell which contains the immobilized oxidoreductases and, if desired, the co-immobilized electron carriers by generating reduction or oxidation equivalents at a suitable voltage and the solution to be purified flows continuously through the cell. In this process it has been found to be advantageous to adjust the residence time of the solution in the cell to 0.2 to 5 cell volumes/minute, preferably 0.5 to 2 cell volumes/minute. In this process the immobilized oxidoreductases and, if desired, the electron carriers are retained in the cell while the excess ions are washed from the cell. One preferably uses a system with a separate anode and cathode. The necessary electrolytic connection can for example be accomplished by means of a coarse glass filter. The eluates of both electrodes can be brought together again after the reaction. As a result a neutral pH is again achieved after passage through the total system.

However, there may be areas of application in which it is acceptable to add buffer substances to the aqueous solution which it is intended to purify. In this case a flow cell would be in no way obligatory.

If several reduction or oxidation steps are necessary to convert a substance in aqueous solution (e.g. in the reduction of nitrate) then, as a rule, several different enzymes have to be used which may also, if desired, be co-immobilized with different electron carriers. Therefore a cell can for example contain various enzyme/electron carrier systems each on different carriers. It is, however, also possible to connect several cells in series in which only one enzyme/electron carrier system is then for example present in a cell. The latter method is preferred.

The concentration of the problematic substance in the aqueous solution to be purified or to be analyzed can encompass a wide range. The conditions of the method according to the present invention can also be varied in correspondence with this concentration. At low concentrations of the problematic substances it is possible to use correspondingly smaller cell designs (i.e. smaller amounts of enzyme and, if desired, electron carrier or/and smaller amounts of redox equivalents) or/and is possible to have higher flow rates in a flow cell. At a higher concentration of the problematic substance correspondingly larger cell designs or/and lower flow rates are necessary. Moreover, if the concentrations of the problematic substances are too high then they can be lowered to suitable values by dilution with water. The concentration range for the application of the method according to the present invention is preferably from 0.01 mmol/l to about 10 mmol/l whereby values which lie above or below this are also not excluded.

The potential difference in the electrolysis cell must be determined according to the oxidoreductases used. Thus in the reduction of nitrate it turns out that the reductases are inactivated within a certain time period at a voltage of over 4 volts. In contrast, the oxidation of methanol in the presence of alcohol oxidase can be carried out at a voltage of over 10 volts.

The present invention in addition concerns a potentiometric cell for converting reducible or oxidizable substances in aqueous solution which contains an electrode body and immobilized oxidoreductases and, if desired, co-immobilized electron carriers. In this case the form of the electrode body may be selected as desired. It may be thread-like or shaped like a band (spiral, linear), a spirally wound foil, it may also be a massive electrode with borings, or arrangements of stacked frits or woven nets. Preferred embodiments of the electrode body according to the present invention are shown in FIGS. 3 to 8.

FIG. 3 and 4 show electrodes formed in the shape of wires or bands which extend spirally (FIG. 3) or straight (FIG. 4) through a matrix containing enzyme which is composed of fine-grained carrier material. FIG. 5 and 6 show one-piece electrodes which are embedded in a matrix containing enzyme in which the electrodes are either in the form of a perforated block (FIG. 5) or as a spirally wound foil (FIG. 6). FIG. 7 and 8 show multi-component electrodes which can be in the form of frits stacked on top of one another (FIG. 7) or nets (FIG. 8).

Oxidoreductases and the electron carriers which may be present in the cell according to the present invention are for example immobilized directly on the carrier material by cross-linking or via a spacer by means of an epoxy, cyanogen bromide, diisocyanate, carbodiimide glutardialdehyde, EDC or FMP compound. If a semiconductor material such as e.g. silicon or graphite is used as the electrode body then the oxidoreductases and, if desired, electron carriers can be immobilized directly on the surface of the electrode body.

As an alternative to this, polymers of natural material or plastics can be used as the carrier material which provide several chemically different binding sites at defined intervals (e.g. they are bifunctional) so that enzymes and electron carriers can be bound alternately directly adjacent to one another in molecular vicinity. The aim is that these polymers can conduct a current. When the oxidoreductase and, if desired, the electron carriers are immobilized directly on the electrode, reduction or oxidation equivalents can be transferred directly from the electrode body onto the oxidoreductases or, if desired, onto the electron carriers without the necessity for an electrolysis of the water (i.e. the reaction could take place below the water potential of 1.28 volts).

Otherwise the immobilization takes place on a suitable carrier material or a mixture of suitable carrier materials (see above) which are not a constituent of the electrode body.

In this case the solid carrier material is preferably in a finely dispersed form so that the electrode body can be embedded in the carrier material (see e.g. FIGS. 3 to 8). One can also use a type of metal foam as the electrode body in which the finely-dispersed carrier material containing the enzymes and, if desired, electron carriers in an immobilized form is located in its pores or holes. Such a foam-like material can for example be composed of a package of perforated foils or metal nets in which the carrier particles would then be located in the pores or holes of the nets or foils.

The cell according to the present invention is preferably in the form of a flow cell. For this the cell can for example be bounded on two facing sides by glass frits. Then the aqueous liquid which is to be purified flows through the space formed by the cell at an adjustable rate so that a shift in pH which could cause an inactivation of the enzymes is avoided.

The present invention in addition concerns the use of the potentiometric cell according to the present invention for converting reducible or oxidizable substances in drinking water or waste water. In particular the cell according to the present invention can be used to convert i.e. to determine and in particular to remove nitrate, methanol or halogenated hydrocarbons.

BRIEF DESCRIPTION OF DRAWINGS

It is intended to further elucidate the present invention by the following examples in conjunction with FIGS. 1 to 8.

FIG. 1 shows an apparatus according to the present invention with immobilized enzyme and electron carrier and an electrode for the reduction of nitrate to nitrite, FIGS. 3($a$ and $b$) shows a potentiometric cell with an electrode body formed in a spiral shape which is embedded in a matrix containing enzyme whereby FIG. 3$a$ shows a longitudinal section

EXAMPLE 1

Figure 1:
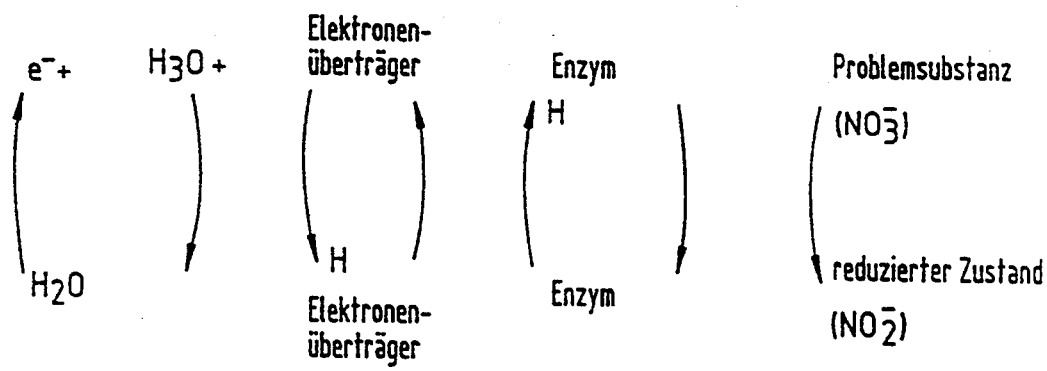
FIG. 1. Shows a schematic representation of the course of a reduction using the reduction of nitrate to nitrite as an example.
Figure 2:
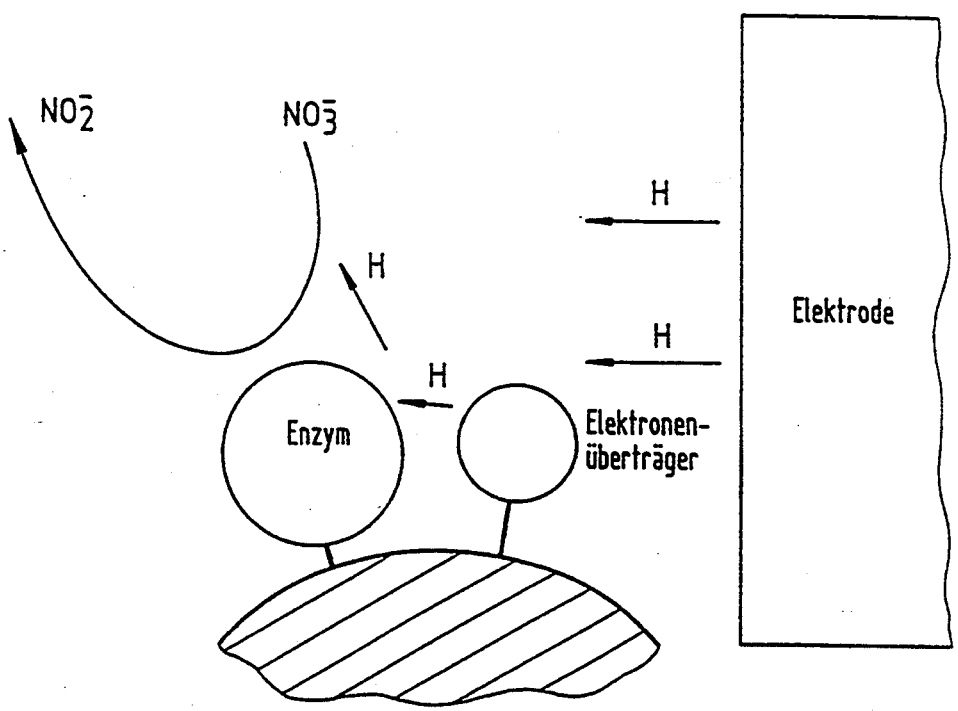
Figure 3A:
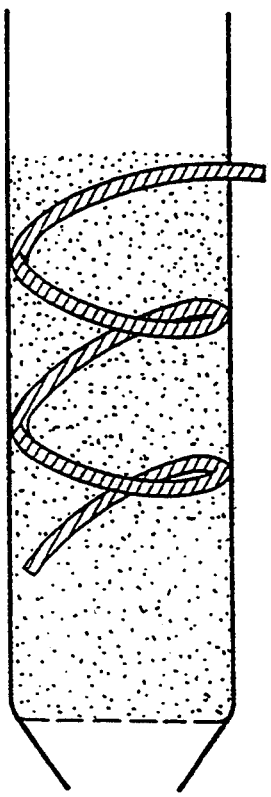
FIG. 3b shows a cross-section through the cell, FIGS. 4($a$ and $b$) a potentiometric cell with a wire-like straight electrode body which is embedded in a matrix containing enzyme, FIGS. 5($a$ and $b$) shows a potentiometric cell with a one-piece electrode body formed as a permeated block which is embedded in a matrix containing enzyme, FIGS. 6($a$ and $b$) shows a potentiometric cell with a one-piece electrode body formed as a spirally wound foil which is embedded in a matrix containing enzyme, FIGS. 7($a$ and $b$) shows a potentiometric cell with a multi-component electrode body comprising frits stacked one top of one another which is embedded in a matrix containing enzyme, FIG. 8($a$ and $b$) shows a potentiometric cell with a multi-component electrode body comprising nets stacked on top of one another which is embedded in a matrix containing enzyme.
Figure 4A:
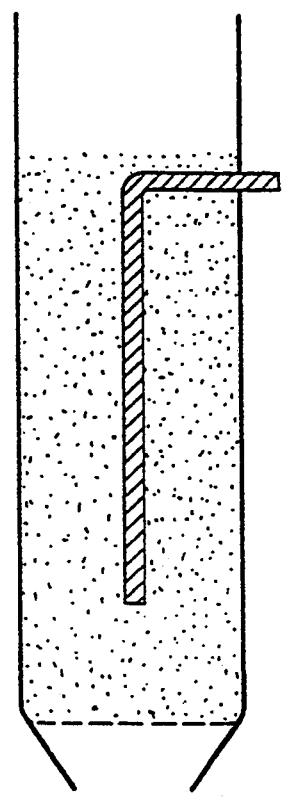
Figure 3B:
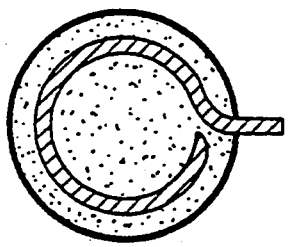
Figure 4B:
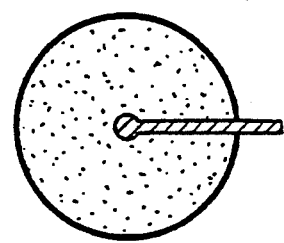
Figure 5A:
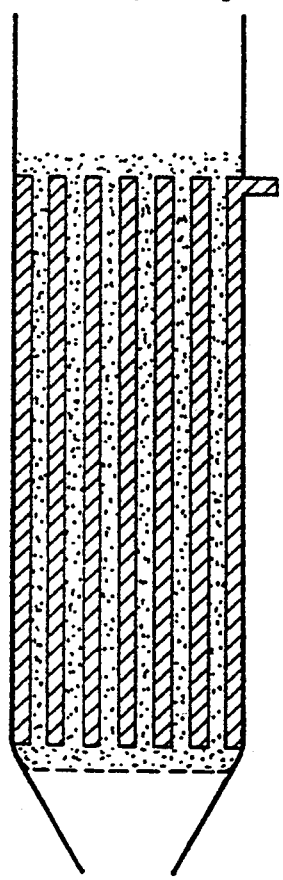
Figure 6A:
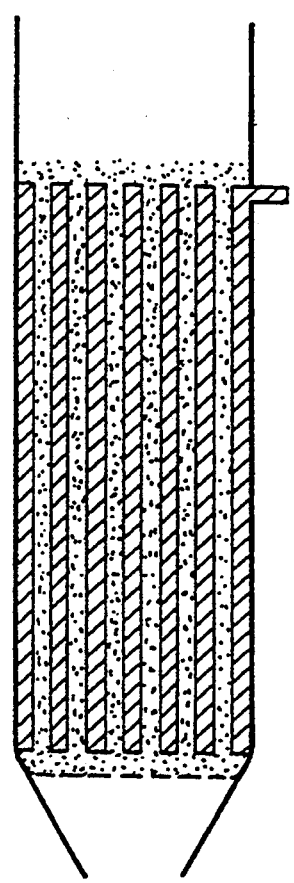
Figure 5B:
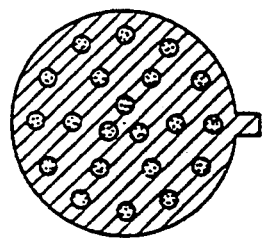
Figure 6B:
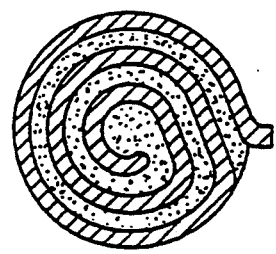
Figure 7A:
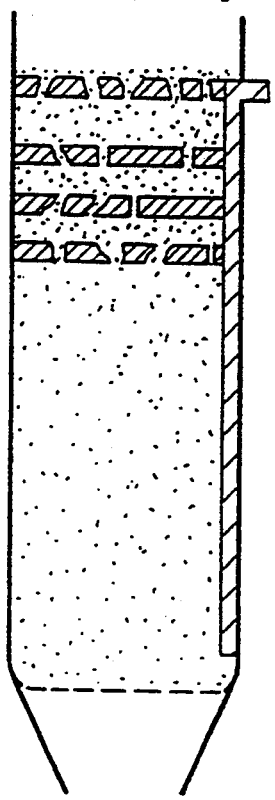
Figure 8A:
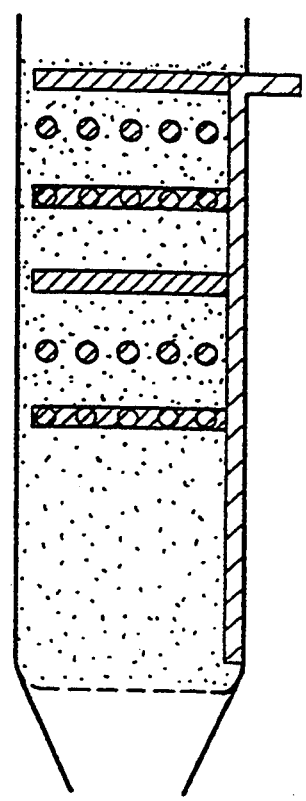
Figure 7B:
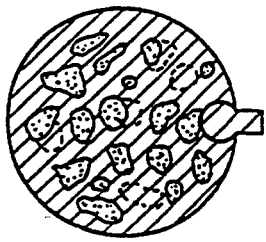
Figure 8B:
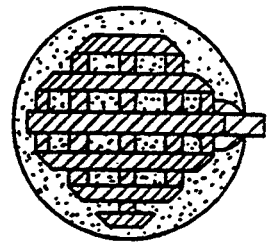

Degradation of nitrate to nitrogen 1.1 Selection of suitable enzymes and electron carriers The reduction of nitrate to nitrogen takes place in three steps. In the first step nitrate is reduced by nitrate reductase to nitrite. In the second step nitrite is reduced by nitrite reductase to $N_2O$ and in the third step $N_2O$ is reduced by $N_2O$ reductase to $N_2$.

Nitrate reductases from Aspergillus and maize (Zea mays) as well as a mixture of nitrite reductases and $N_2O$ reductases from Rhodopseudomonas sphaeroides were examined. The nitrate reductase from Aspergillus was obtained from Boehringer Mannheim. Immunoaffinity-chromatographically pure nitrate reductase from maize was produced as described by Ruoff et al. (1989), Biochem. Biophys. Res. Commun. 161, 496–501. Both enzymes were freeze-dried before use.

Firstly the enzyme activity of the free enzymes was tested with immobilized dyes (as electron carriers) in comparison to the free dyes. In this case the activity of the free enzyme in combination with the free dye methyl viologen was set as 100 %. Sodium dithionite was used as the reducing agent.

A standard reaction contained 2.5 μmol $KNO_3$ in 0.5 ml 50 mmol/ml Na, K phosphate buffer pH 7.2. 1.5 μmol dye was mixed with 100 m units enzyme and the reaction was started in the presence of 20 μl 10 % sodium dithionite (in 50 μg/ml $NaHCO_3$). After a 15 minute incubation at 25° C. the reaction mixture was reoxidized by vigorous shaking and the nitrite was determined by the Griess-Ilosvay reaction (Kundu and Nikolas (1985), Arch. Microbiol. 141, 57–62). The reaction was carried out in tightly stoppered 1.5 ml reaction vessels. Controls contained either no dye or heat-inactivated enzyme. 1 unit enzyme reduces 1 μmol nitrate per minute in the presence of 3 μmol/ml methyl viologen. The results of this test are shown in the following Table 1.

TABLE 1

| Dye | Nitrate reductase | | Nitrite reductase |
| --- | --- | --- | --- |
|  | Zea | Aspergillus |  |
| Azure A | 30.8 | 9.7 | 71.9 |
| Cibacron blue | 38.6 | 48.6 | 91.0 |
| Cresyl violet | 13.0 | 2.0 | 84.9 |
| Nile blue | 10.0 | 16.5 | 66.5 |
| Neutral red | 55.0 | 10.8 | 94.5 |
| Safranin T | 44.5 | 4.1 | 66.2 |
| Thionine | 14.5 | 15.9 | 62.6 |
| Bromophenol blue | 21.5 | 8.4 | 58.3 |
| Curcumin | 51.4 | NT | 116.4 |
| Patent blue V | 36.8 | NT | 112.0 |
| Quinoline yellow | NT | NT | 121.8 |

NT = not tested

Subsequently the activity of the immobilized enzyme with the stated co-immobilized dye was determined in relation to the enzyme activity of the immobilized enzyme in the presence of the free dye methyl viologen. Sodium dithionite was used as the reducing agent. The results are shown in the following Table 2.

TABLE 2

| Reductases: | A | B | C |
| --- | --- | --- | --- |
| Dyes: |  |  |  |
| Azure A | 97.6 | 33.1 | 62.5 |
| Cibacron blue | 20.4 | 50.1 | 55.3 |
| Neutral red | 16.4 | 8.7 | 102.0 |
| Safranin T | 75.0 | 3.0 | NT |
| Bromophenol blue | 93.6 | NT | 50.0 |
| Curcumin | 109.7 | NT | 97.3 |
| Patent blue V | 112.2 | NT | 105.2 |
| Quinoline yellow | NT | NT | 113.5 |

A = Zea nitrate reductase
B = Aspergillus nitrate reductase
C = Rhodopseudomonas nitrite reductase
NT = not tested A = Zea nitrate reductase
B = Aspergillus nitrate reductase
C = Rhodopseudomonas nitrite reductase
NT = not tested It can be seen from Tables 1 and 2 that the properties of the enzyme and dye system can be considerably changed by the immobilization. The dyes Azure A, bromophenol blue, curcumin and patent blue V are particularly suitable for the nitrate reductase from maize (Zea mays), whereas the dyes neutral red, curcumin, patent blue V and quinoline yellow are particularly suitable for the nitrite reductase from Rhodopseudomonas.

1.2 Procedure for nitrate degradation

A 1 ml reactor cell containing co-immobilized nitrate reductase and azure A is connected to another 1 ml reactor cell containing immobilized nitrite reductase and $N_2O$ reductase together with co-immobilized neutral red. The two reactor cells were connected in series. Two different substrate concentrations were investigated:

a) high concentration 10 ml of a 10 mmol/1 nitrate solution was passed through both columns (connected in series) at a flow rate of 1 ml/min and a voltage of 4V. The nitrate and nitrite concentrations measured in the eluate are listed in Table 3. According to this the columns reduced 1.272 μmol oxidized nitrogen/min.

b) low concentration

The above experiment was repeated with 10 ml of a 1 mmol/1 nitrate solution. Neither nitrate nor nitrite was detectable in the eluate. Moreover no NO and no $N_2O$ (detectable as $HNO_2$ after reoxidation with oxygen gas) could be detected in the eluate (Table 3).

TABLE 3

|  | Concentration (mmol) | | |
| --- | --- | --- | --- |
|  | $NO_3^-$ | $NO_2^-$ | $NO/N_2O$ |
| 1. high $NO_3^-$ concentration | | | |
| (solution) | 10.0 | 0 | 0 |
| (eluate) | 8.69 | 0.38 | 0 |
| 2. low $NO_3^-$ concentration | | | |
| (solution) | 1.0 | 0 | 0 |
| (eluate) | 0 | 0 | 0 |

EXAMPLE 2

Methanol degradation by alcohol oxidase

Alcohol oxidase (EC 1.1.3.13) from yeast (Saccharomyces) is a flavoprotein which already contains an electron-transferring cofactor. Thus in this case a co-immobilization of an electron carrier (dye) is not necessary. During the degradation of methanol formaldehyde is formed.

38 units of alcohol oxidase were immobilized on Fractogel HSK and examined in an electrochemical reactor cell. The enzymatic activity in 10 mmol/1 phosphate buffer with methanol as the substrate was set to 100 %. Before the actual experiment the reaction mixture was reduced with dithionite in order to remove atmospheric oxygen. In this state only 13 units (34 %) activity were measured. Subsequently the reactor cell was poled in such a way that oxidizing conditions prevailed in the enzyme region. At 12V and 1 mA in the cell, 21.9 units (58 %) activity were measured.

This result shows that even without co-immobilized electron carriers the immobilized alcohol oxidase is apparently able to take up electrons from substrates and to transfer them onto an electrolytically generated oxidizing agent.

We claim:

1. Method for the conversion of reducible or oxidizable substances in aqueous solution, which comprises:
passing an aqueous solution containing said substances through a housing having operatively associated therewith an electrode body and into effective contact with:
at least one immobilized oxidoreductase selected from the group consisting of nitrate-oxidoreductase, nitrite-oxidoreductase, and $N_2O$-oxidoreductase,
which is in effective contact with at least one co-immobilized electron carrier which simultaneously supplies reduction or oxidation equivalents to said oxidoreductase, under conditions supportive of the conversion of said substances; and recovering water having less of said reducible or oxidizable substances than were in said aqueous solution.

2. Method as claimed in claim 1, further including contacting said oxidoreductase with an immobilized electron carrier in direct molecular vicinity or/and bound directly together with said oxidoreductase.

3. Method as claimed in claim 2, wherein said electron carrier comprises a non-toxic dye.

4. Method as claimed in claim 2 wherein said oxidoreductase and said electron carrier are immobilized on a solid carrier material and are in direct molecular vicinity or/and are bound directly together.

5. Method as claimed in 1, wherein atomic hydrogen is used as the reduction equivalent.

6. Method as claimed in 1, wherein atomic oxygen is used as the oxidation equivalent.

7. Method as claimed in claim 1, wherein reduction or oxidation equivalents are generated in a potentiometric cell which contains the immobilized oxidoreductases as well as the co-immobilized electron carriers and the solution to be purified flows continuously through the cell.

8. Method as claimed in claim 7, wherein the residence time of the solution in the cell is about 0.2 to 5 cell volumes/min.

9. Method as claimed in claim 7, wherein said potentiometric cell comprises separate cathode and anode regions and the solutions which flow from both regions are recombined.

10. Method as claimed in claim 7, including connecting several cells in series.

11. Method as claimed in claim 10, comprising passing said solution through a multiplicity of different individual cells contain different immobilized oxidoreductases.

12. Method as claimed in claim 1, wherein said substances to be converted are selected from the group comprising
   (a) inorganic salts, and
   (b) organic compounds.

13. Method as claimed in claim 12, wherein a compound comprising a nitrate group is converted in aqueous solution.

14. Method as claimed in claim 12, wherein methanol is converted in aqueous solution.

15. Method as claimed in claim 12, wherein halogenated hydrocarbons are converted in aqueous solution.

16. Method as claimed in claim 12 wherein said inorganic salt is at least one member of the group of nitrate, sulfate, cyanide, sulfide and phosphate.

17. Method as claimed in claim 12 wherein said organic compound is at least one member of the group of aromatic hydrocarbons, halogenated hydrocarbons, organophosphorus compounds, alcohols, ketones, phenols and detergents.

18. Method as claimed in claim 1, wherein the water of said aqueous solution is drinking water or waste water.

19. Method as claimed in claim 1, wherein the concentration of the substances to be converted in the aqueous solution is about 0.01 mmol/l to about 10 mmol/l.

20. Method as claimed in claim 1 including supplying reduction or oxidation equivalents by electrolysis.

21. Method as claimed in claim 20, including generating said reduction or oxidation equivalents by electrolysis of water.

22. A potentiometric cell for converting reducible or oxidizable substances in an aqueous solution comprising:

a housing including means to permit said aqueous solution to flow therethrough;

an electrode body operatively associated with said housing;

at least one immobilized oxidoreductase, selected from the group consisting of nitrate-oxidoreductase, nitrite-oxido-reductase, and $N_2O$-oxidoreductase, so positioned as to be in operative association with aqueous solution flowing through said housing;

at least one co-immobilized electron carrier operatively associated with said oxidoreductase by being so positioned as to be in direct molecular vicinity of, and/or bound directly together with, said oxidoreductase, and so positioned as to be in operative association with said aqueous solution flowing through said housing;

means to introduce an aqueous solution containing said oxidizable or reducible substance in need of conversion into said housing;

means to cause said aqueous solution to flow through said housing in operative association with said immobilized oxidoreductase and said co-immobilized electron carrier under conditions supportive of the conversion of said oxidizable and/or reducible substances with said oxidoreductase; and means to recover a product comprising water and less of said oxidizable and/or reducible substances than was present in said fed aqueous solution from said housing.

23. Process of converting polluted water intended for drinking into potable water, or environmentally unacceptable waste water into an environmentally acceptable condition which comprises passing such water through a potentiometric cell as claimed in claim 22 and converting reducible or oxidizable substances in said water, in said cell.

24. Process as claimed in claim 23 wherein said water contains a nitrate.

25. Process as claimed in claim 23 wherein said water contains methanol.

26. Process as claimed in claim 23 wherein said water contains halogenated hydrocarbons.

* * * * *